United States Patent [19]
Macquet

[11] 4,452,812
[45] Jun. 5, 1984

[54] ORGANIC COMPLEX OF PLATINUM, ITS PREPARATION AND ITS USE FOR TREATING MALIGNANT TUMORS

[75] Inventor: Jean-Pierre Macquet, Auzeville, France

[73] Assignee: Sanofi, Paris, France

[21] Appl. No.: 257,939

[22] Filed: Apr. 27, 1981

[30] Foreign Application Priority Data

Apr. 28, 1980 [GB] United Kingdom ............... 8014109

[51] Int. Cl.$^3$ ............ C07F 15/00; A01N 55/02; A61K 31/28
[52] U.S. Cl. ............................ 424/287; 260/429 R
[58] Field of Search ................... 260/429 R; 424/287

[56] References Cited

U.S. PATENT DOCUMENTS 4,115,418 9/1978 Gale et al. ............... 260/429 R
4,140,707 2/1979 Cleare et al. ............ 260/429 R
4,203,912 5/1980 Hydes et al. ............ 260/429 R
4,225,529 9/1980 Hydes et al. ............ 260/429 R
4,228,090 10/1980 Hydes et al. ........... 260/429 R

OTHER PUBLICATIONS

Cleare, Coordination Chemistry Revues, 12, pp. 349–360 (1974).
Leh et al., J. of Pharmaceutical Sciences, V65, No. 3, pp. 318 & 319 (1976).

Primary Examiner—Helen M. S. Sneed
Attorney, Agent, or Firm—Weiser, Stapler & Kimmelman

[57] ABSTRACT

An organic complex of platinum, cis-isocitrato (1,2 diaminocyclohexane) platinum (II) having improved anti-tumor activity and water-solubility. The complex is prepared by reacting cis-dichloro (1,2-diaminocyclohexane) platinum (II) with silver nitrate, removing the silver chloride formed, and reacting the resulting liquid with trisodium isocitrate. The complex is administered in the form of a pharmaceutical composition.

20 Claims, 4 Drawing Figures

ORGANIC COMPLEX OF PLATINUM, ITS PREPARATION AND ITS USE FOR TREATING MALIGNANT TUMORS

This invention relates to an organic complex of platinum, a process for preparing it and its therapeutic use for the treatment of malignant tumours.

According to one aspect of the invention, there is provided as a novel chemotherapeutic agent having anti-tumour activity cis-isocitrato (1,2-diaminocyclohexane) platinum (II), which may be abbreviated to PHIC. This organic complex of platinum can be prepared by reacting a molecular moiety in which the platinum atom is partially chelated with 1,2-diaminocyclohexane (trans-d and l isomers) represented by the general formula:

(1)

with trisodium isocitrate (dl isomer), which has the formula:

(2)

which acts as a labile ligand, and thereafter recovering the resulting platinum complex from the reaction mixture. Two bonds can be formed between molecule (1) and any pair of reactive positions 1, 2, 3 and 4 of the molecule (2). Chelation most likely occurs at the 1- and 2-positions and at the 1- and 3-positions. Interaction at the 1-4 3-4, 2-3 and 2-4 positions is also possible. A monodentate interaction between (1) and (2) is also quite possible: the first Pt bond being a Pt-carboxylato bond, the second being a Pt—OH bond. The invention includes all possible complexes as well as mixtures of these complexes in all proportions.

In a preferred embodiment of the invention, the organic complex of platinum is prepared by reacting cis-dichloro (1,2-diaminocyclohexane) platinum (II) with silver nitrate to form the corresponding dinitrato platinum compound which is thereafter reacted with trisodium isocitrate to form the required platinum complex.

The platinum complex of the invention, i.e. PHIC, has been found to have useful anti-tumor activity. It is useful in the treatment of malignant tumors in warm blooded animals including humans. Apart from its anti-tumor activity, PHIC has also been found to exhibit anti-microbial activity and to be useful as a disinfectant.

Thus in accordance with another aspect of the invention, there is provided a method of treating malignant tumours in a human subject comprising the administration to the subject of an effective dose of PHIC.

It will be appreciated that for chemotherapeutic use, PHIC will normally be administered in the form of a pharmaceutical composition comprising PHIC as an active ingredient in association with a pharmaceutically acceptable diluent or excipient therefor. For the treatment of malignant tumours, PHIC may be administered orally, intramuscularly or intravenously. Hence the pharmaceutical composition will normally be made up in a form appropriate to the desired mode of administration, preferably in a dosage unit form containing a discrete amount of the active ingredient PHIC. For oral administration the dosage unit may be, for example, a capsule, pellet or packaged powder, whereas for intravenous or intramuscular administration, the dosage unit may be, for example, a discrete quantity of an injectable solution or suspension packaged in a suitable sterile container, such as an ampoule.

For the treatment of malignant tumours, the daily dosage of PHIC will generally be from about 1 to about 400 mg per kilogram body weight of the treated subject. It may be administered in one or several administrations.

The inhibition of cellular proliferation by, and the anti-tumor activity of, platinum coordination complexes, in particular cis-dichlorodiammine platinum (II), which may be abbreviated to PDD, of the formula:

were discovered some fifteen years ago. Since that time, much research has been devoted to this category of compound in the hope of first, identifying the most active members, and second, of overcoming the disadvantages which were rapidly found to present, these compounds as known to in particular, their low degree of solubility which renders administration difficult, their nephrotoxicity and ototoxicity. Research has also been done to elucidate their mechanism of action. Recent studies have shown that the solubility of these compounds, their anti-tumor activity and their nephrotoxic effects can be favourably influenced by causing various alterations into the molecule. For instance, the replacement of the two chlorine atoms in PDD by bidentate ligands such as oxalato and malonato, was proposed as early as 1973. Then, in 1974, the replacement of the two $NH_3$ molecules in PDD by 1,2-diaminocyclohexane was suggested. The complex so obtained had the advantage of not causing any cross-resistance to PDD in the animal treated.

However, these investigations were not pursued because of the low water solubility of all these compounds. Research was thus directed to ligands possessing a third carboxylic group which could enhance solubility of the complex and possibly improve its therapeutic activity without necessarily increasing its toxicity.

These ligands include sodium trans-aconitate and sodium citrate molecules, the latter being present in the living human organism (Krebs cycle) in both the citric and isocitric isomeric forms. Different corresponding complexes have been synthesised in order to compare their properties as will be described below. It was observed that the citrate complex PHIC exhibited a greater solubility than compound (3).

The present invention is concerned with the behaviour and properties of the isocitrate complex, PHIC. In comparison with all the compounds prepared both in previous investigations and in the course of the present study, this isocitrate complex presents the following unexpected advantages:

1. An almost unlimited degree of solubility which is at least several hundred times greater than that of other similar platinum complexes.
2. Extremely low toxicity in mice and baboons.
3. Very marked anti-tumor activity toward L1210 leukemia and sarcoma 180.

The comparative trials described below quantitate these advantages, demonstrate this outstanding combination of properties and consequently show the therapeutic value of this compound in the treatment of tumours.

These comparative studies were undertaken with the following compounds which are identified by abbreviations for greater convenience:

I. COMPOUNDS SYNTHESISED FROM CIS-DICHLORODIAMINE PLATINUM (II) OR PDD OF FORMULA

PAC: cis-citratodiammineplatinum (II)
PAIC: cis-isocitratodiammineplatinum (II)
PATA: cis-(t-aconitato) diammineplatinum (II)

II. COMPOUNDS SYNTHESISED FROM CIS-DICHLORO(1,2-DIAMINOCYCLOHEXANE) PLATINUM (II) OR DIS-Pt (DAC) Cl₂ OR PHD

PHC: cis-citrato (1,2-diaminocyclohexane) platinum (II)
PHIC: cis-isocitrato (1,2-diaminocyclohexane) platinum (II)
PHTA: cis-(t-aconitato) (1,2-diaminocyclohexane) platinum (II)

The compound of the invention, i.e. PHIC, can be prepared from compound (4) as follows:

In the first step, the dihydrate derivative was prepared in accordance with the following reaction:

In the second step, the isocitrate anion was complexed as follows:

The following Example illustates the preparation of PHIC.

EXAMPLE

In 250 ml of bidistilled water were suspended 5 g of cis-Pt (DAC)Cl₂ and 4.3 g of silver nitrate were added. The reaction medium was protected from light. The reaction itself took place at 50°–55° C. over a period of 4 hours. A white precipitate of silver chloride formed. The reaction medium was then brought to 0°–4° C. for several hours and then filtered on Whatman paper. (The word "Whatman" is a registered Trademark of Whatman Inc., New Jersey, U.S.A.). The precipitate was washed with water (50–75 ml) and the resulting colorless filtrate (300–350 ml) was passed through a Millipore filter (0.45 microns). (The word "Millipore" is a registered Trademark of the Millipore Corporation, Massachusetts, U.S.A.). To the filtrate, 3.85 g of trisodium isocitrate, 2H₂O were added and the mixture was brought to 60°–65° C. for 20 hours during which time it was shielded from light. The resulting yellow-colored solution (which can be filtered on Whatman paper if necessary) was then concentrated to 25–30 ml using a rotavapor (temperature of the bath =50° C.).

The resulting complex was filtered on a Millipore filter (0.45 microns) and added by means of a pipette to 1000 ml of 1/1 cold ethanol/acetone mixture under continuous stirring. The medium was allowed to stand at 4° C. for 2 hours, then filtered on sintered glass, washed with 100 ml acetone and then with 100 ml ether.

The off-white complex obtained was dried under vacuum and then weighed. In this manner, about 6.5 g of PHIC were collected from 5 g of cis-Pt (DAC)Cl₂, which corresponds to a yield of 85%.

The PHIC so obtained was in the form of a fine off-white powder which began to turn black when heated to 245° and then completely decomposed at 254° C. The following results were obtained in the elementary analysis of PHIC (Pt was determined by atomic absorption):

|  | C | H | N | Pt | Cl | Na |
|---|---|---|---|---|---|---|
| PHIC.3H₂O calculated | 24.26 | 4.10 | 4.72 | 32.84 | — | 7.16 |
| M.W. = 594.10 found | 24.10 | 3.96 | 4.76 | 32.10 | — | 6.99 |

These analytical results are also in agreement with the formula PHIC.2H₂O in which the Pt (DAC) moiety does not form two bonds with the isocitrate ion, but is linked with one carboxylate ion, most likely C-1, the other bond being a Pt—OH bond.

This compound has an exceptionally high degree of solubility. In water it is almost unlimited (more than 1500 mg/ml). In a 9% solution of sodium chloride it is about 700 mg/ml, the complex changing in 24 hours to a yellow chlorinated derivative which precipitates. PHIC can be identified by its chromatogram and its spectrum analysis (U.V., I.R. and ¹³C) which are illustrated in the accompanying drawings.

Figure 1:
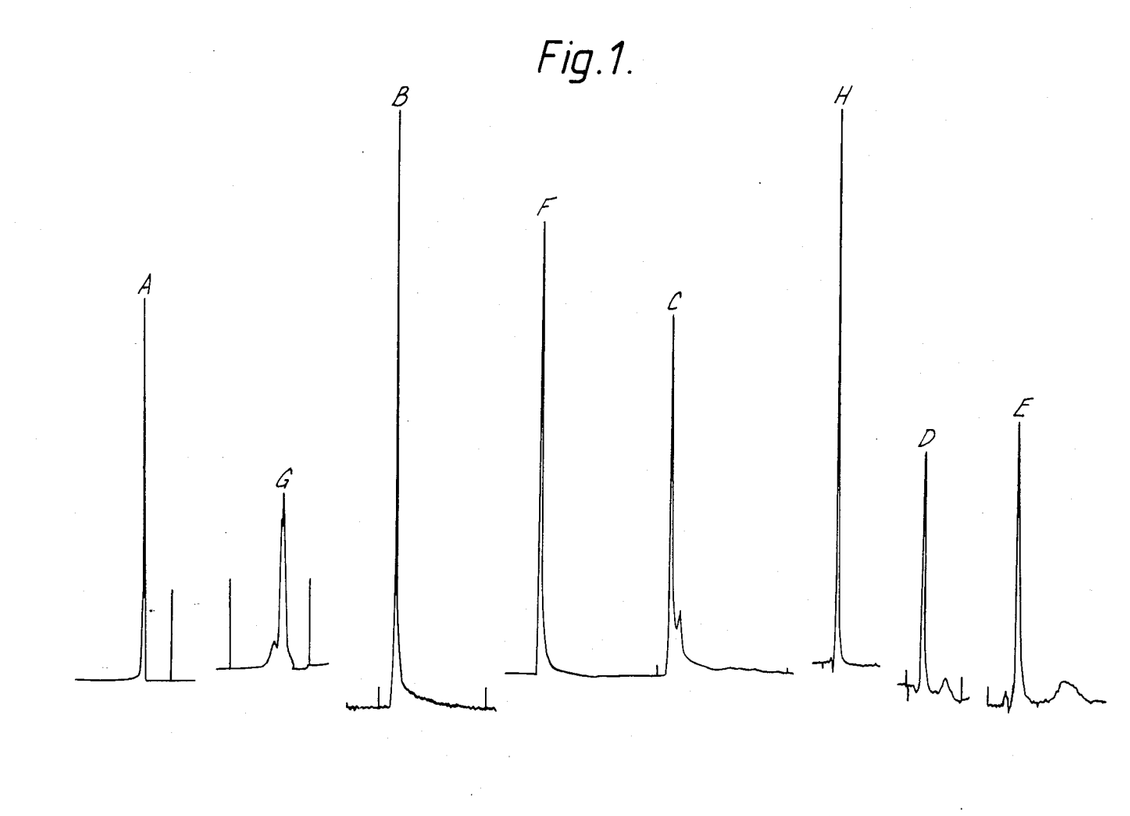

In FIG. 1 are shown the high pressure liquid chromatograms of the following compounds:
A: PDD
B, C, D and E: PHIC
F and H: trisodium isocitrate
G: PAC
obtained under the following experimental conditions:

| Compound | Concentration of the Solvent | Volume Injected (μl) | Sensitivity | Eluent | Flow rate (ml/min) | Pressure (psi) |
|---|---|---|---|---|---|---|
| A. PDD | 0.5 mg/ml 9% NaCl sol. | 25 | 0.01 | 9% NaCl solun | 1.5 | 1500 |
| B. PHIC | 0.5 mg/ml | 25 | 0.02 | H₂O | 1.5 | 1500 |

-continued

| Compound | Concentration of the Solvent | Volume Injected (μl) | Sensitivity | Eluent | Flow rate (ml/min) | Pressure (psi) |
|---|---|---|---|---|---|---|
| C. PHIC* | $H_2O$ 0.5 mg/ml $C_2H_5OH/H_2O$ (4/6) | 15 | 0.04 | $C_2H_5OH/H_2O$ (4/6) | 2 | 300 |
| D. PHIC* | 0.5 mg/ml 1% acetic acid | 50 | 0.01 | 1% acetic acid | 4 | 300 |
| E. PHIC* | 0.5 mg/ml 1% acetic acid | 50 | 0.01 | 1% acetic acid | 2 | 300 |
| F. ISOCITRATE* | 3 mg/ml $C_2H_5OH/H_2O$ (4/6) | 10 | 0.04 | $C_2H_5OH/H_2O$ (4/6) | 2 | 300 |
| G. PAC | 5 mg/ml $H_2O$ | 20 | 0.5 | $H_2O$ | 1.3 | 1000 |
| H. ISOCITRATE* | 5 mg/ml 1% acetic acid | 10 | 0.4 | 1% acetic acid | 4 | 300 |

*column $C_{18}$ radial reverse

Figure 2:
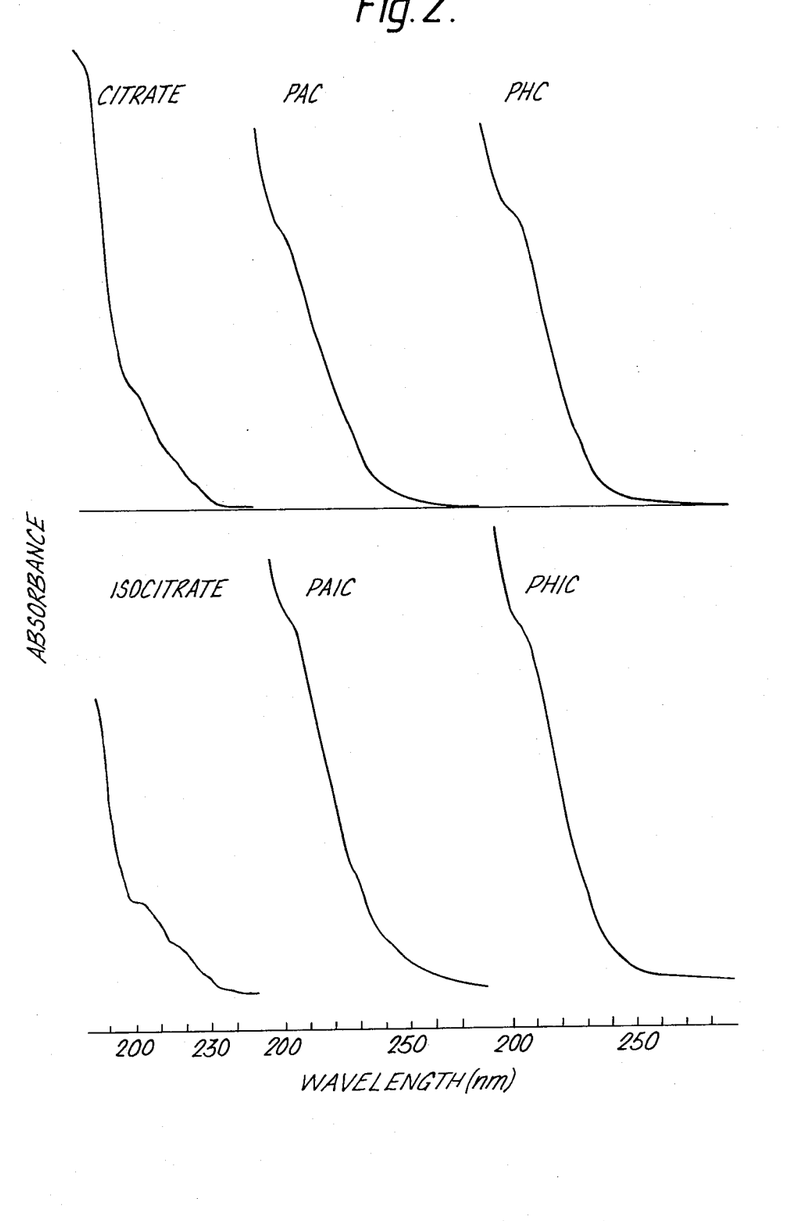
Figure 3:
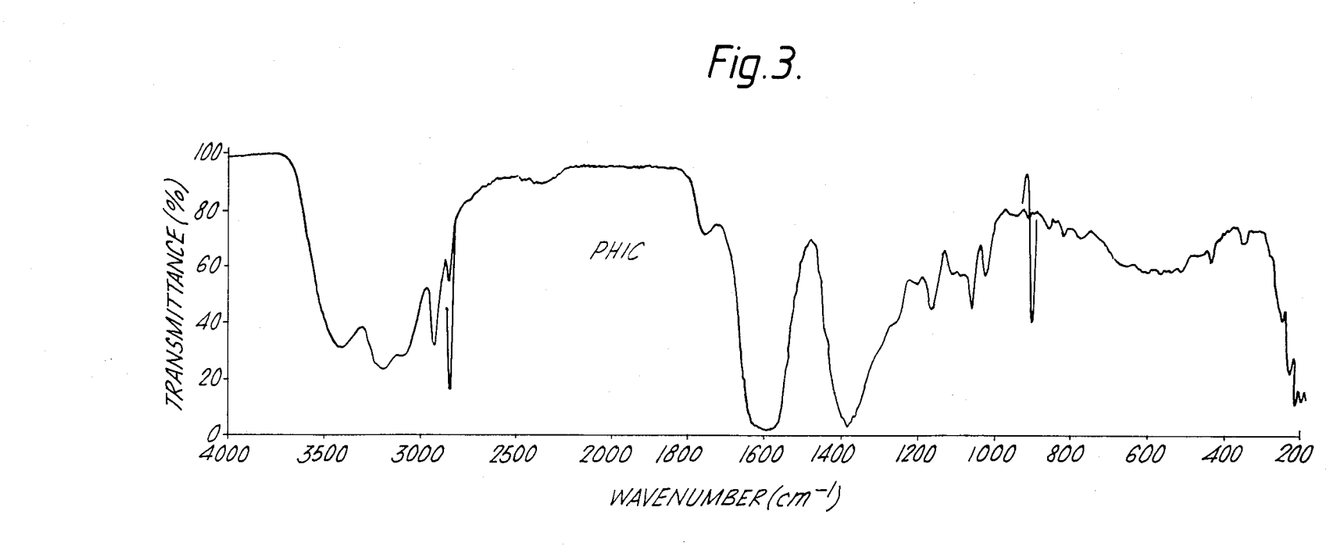

In FIG. 2 are shown the U.V. spectra of the indicated compounds namely:
- trisodium citrate
- PAC
- PHC
- trisodium isocitrate
- PAIC
- PHIC obtained under the following experimental conditions:

The U.V. spectra were recorded on a CARY 14 spectrophotometer. All of the complexes as well as the unreacted ligands absorbed between 203 and 204 nm. The concentrations and molecular absorption coefficients $\epsilon$ in l. $mol^{-1}.cm^{-1}$) were the following:
- trisodium citrate: 10 mg/100 ml $H_2O$; $\epsilon = 590$
- PAC: 2.5 mg/100 ml $H_2O$; $\epsilon = 7500$
- PHC: 2.5 mg/100 ml $H_2O$; $\epsilon = 10100$
- trisodium isocitrate: 6 mg/100 ml $H_2O$; $\epsilon = 620$
- PAIC: 3 mg/100 ml $H_2O$; $\epsilon = 6200$
- PHIC: 3 mg/100 ml $H_2O$; $\epsilon = 9400$ In FIG. 3 is shown the I.R. spectrum of PHIC recorded on a Perkin Elmer 577 spectrophotometer. The solid compound was diluted to 1% with potassium bromide and compressed into pellets. The two standard peaks correspond to $\nu_1 = 2850.7$ $cm^{-1}$ and $\nu_2 = 906.7$ $cm^{-1}$.

Figure 4:
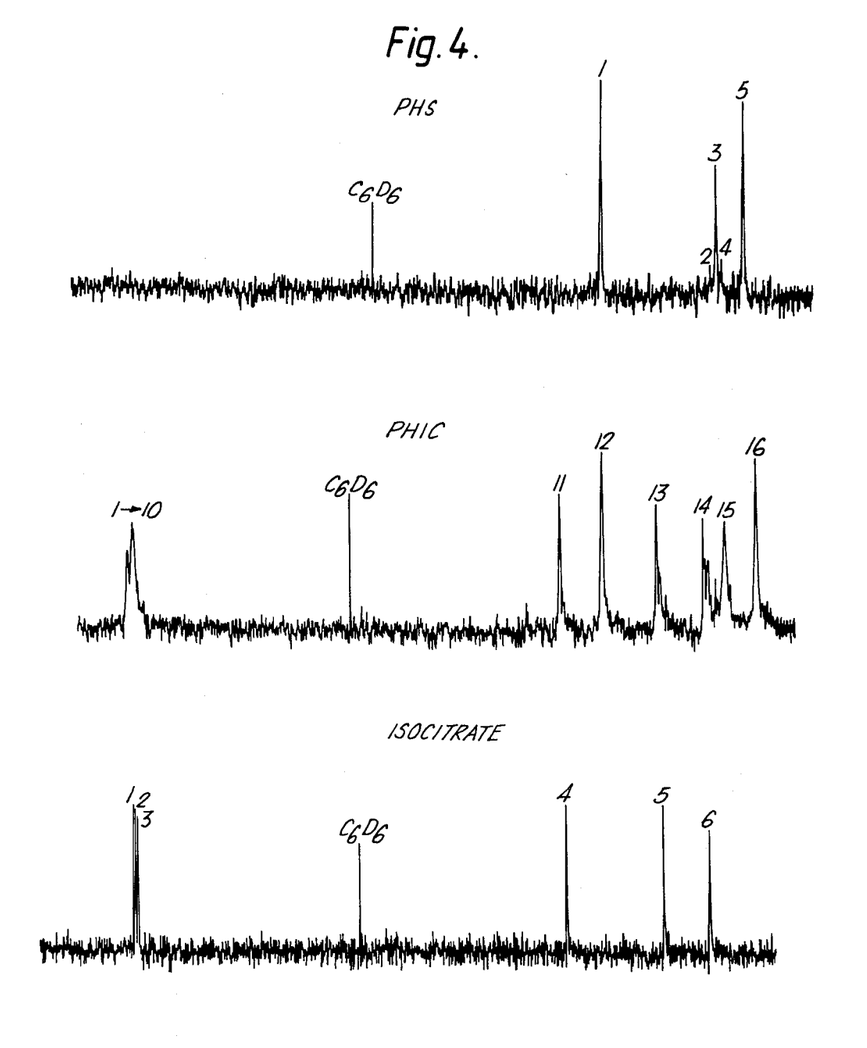

Finally, in FIG. 4 are shown the $^{13}C$ spectra of trisodium isocitrate, PHS and PHIC obtained under the following experimental conditions:

The $^{13}C$ resonance spectra with proton decoupling, were obtained using a pulsed Fourrier Transform apparatus, Brüker WH 90, working at 22.62 MHz. The number of scans was 400 for isocitrate, 3000 for PHS and 17000 for PHIC, with a sweepwidth of 6 KHz and a 8K memory. In all cases a 90° pulse of 12 μs was used with a repetition rate of 3s.

The chemical shifts δ Ci are expressed in ppm and are compared to TMS. The compounds were dissolved in $D_2O$ at the concentration of 1 g/ml for isocitrate, 0.44 g/ml for PHS 1.1 g/ml for PHIC and the solutions were filtered on a Millipore filter (0.45 microns) before the spectrum was recorded. The $C_6D_6$ was used as external standard. The chemical shifts are given in the table below. The PHS was included in the study in order to obtain the $^{13}C$ spectrum of the 1,2-diaminocyclohexane ligand complexed with Pt (II). CHEMICAL SHIFTS δ $^{13}C$ (ppm/TMS) OF ISOCITRATE, PHS AND PHIC

| Peak No | δCi | Assignment | Formula |
|---|---|---|---|
| | | | ISOCITRATE |
| 1 | 183.4 | C-2 | |
| 2 | 183.1 | C-3 | |
| 3 | 182.5 | C-1 | |
| 4 | 75.6 | C-4 | |
| 5 | 51.2 | C-5 | |
| 6 | 39.6 | C-6 | |
| | | | PHS |
| 1 | 69.4 | C-1,1' | |
| 2 | 34.6 | } | |
| 3 | 33.0 | } C-2,2' | |
| 4 | 31.4 | | |
| 5 | 25.5 | C-3,3' | |

| Peak No | δCi | Assignment ligand | Ci |
|---|---|---|---|
| | | PHIC | |
| 1 | 184.2 | | |
| 2 | 183.9 | | |
| 3 | 183.8 | | |
| 4 | 182.9 | | |
| 5 | 182.7 | | |
| 6 | 182.4 | ISO* | C-1,2,3 |
| 7 | 182.3 | | |
| 8 | 182.2 | | |
| 9 | 182.0 | | |
| 10 | 181.9 | | |
| 11 | 75.9 / 75.2 | ISO | C-4 |
| 12 | 64.8 / 64.0 | DAC* | C-1,1' |
| 13 | 51.1 / 50.6 / 50.3 / 48.9 | ISO | C-5 |
| 14 | 39.6 / 39.1 / 38.4 / 36.4 | ISO | C-6 |
| | 34.3 | | |

| | | | |
|---|---|---|---|
| 15 | 34.1 ⎫<br>33.4 ⎬<br>32.8 ⎭ | DAC | C-2,2' |
| 16 | 26.3 | DAC | C-3,3' |

*ISO = isocitrate;
DAC = 1,2-diaminocyclohexane

The anti-tumour properties of PHIC were evaluated, in comparative studies, using classical tests on two kinds of experimental tumours in mice, leukemia L 1210 and sarcoma S 180. The experimental conditions used and the results obtained are described below:

I. LEUKEMIA L 1210: Ascite and Solid

DAB mice/2 females (CNRS, Orleans) of 20 to 22 g
10 mice per dose
i.p.=intraperitoneal route; i.v.=intravenous route; s.c.=subcutaneous route (a) i.p. graft—i.p. treatment
$10^5$ cells were grafted intraperitoneally on $D_0$ and intraperitoneal treatment was carried out 24 hours later, $D_1$, in one single injection.

(b) i.p. graft—i.v. treatment
$10^5$ cells were grafted intraperitoneally on $D_0$ and intravenous treatment in the tail vein was carried out 24 hours later, $D_1$, in one single injection.

(c) s.c. graft—i.p. treatment
$10^6$ cells were grafted under the skin behind the head on $D_0$ and intraperitoneal treatment was carried out in one single injection either on $D_1$ or on $D_4$.

II. SARCOMA S180: ASCITE

Swiss female mice (Evic-Ceba, Bordeaux) of 20 to 22 g
10 mice per dose
$10^6$ cells intraperitoneally grafted on $D_0$
intraperitoneal treatment 24 hours later, $D_1$, in one single injection.

The compounds investigated, namely PHIC, PDD, PAC, PAIC, PHC and PHTA, were dissolved in a 9% solution of sodium chloride. Two other compounds, namely the cis-sulfatomonoaquo(1,2 diaminocyclohexane) platinum (II), abbreviated PHS, and the cis-malonato (1,2 diaminocyclohexane) platinum (II), abbreviated PHM, have already been reported and will be included in this study for comparison purposes. PHD and PHM were suspended in a 4% Klucel (hydroxy propyl cellulose) solution (the word "Klucel" is a registered trademark of Hercules Incorporated, Delaware, U.S.A.).

PHS was dissolved in water because its dissolution in 9% aqueous sodium chloride gave rise almost instantaneously to the formation of a yellow insoluble chlorinated compound, most likely monochlorinated then dichlorinated PHD. The solutions of these compounds were prepared extemporaneously. The increase in life span, ILS (%), were calculated in comparison with the controls by the following formula:

$$ILS = \frac{\text{survival of the treated animals} - \text{survival of the control animals}}{\text{survival of the control animals}} \times 100$$

Deaths were recorded until day 30 for L 1210 tumour and until day 60 for S180 tumour. Survivals were included in the ILS calculation by assigning a 30 day life span in the L 1210 experiments and a 60 day life span in the S 180 experiments It should be added that most of the mice reaching 30 days of survival treatment with PHM and PHIC developed peritonitis as PHM and PHIC developed peritonitis as judged by adhesion and hardening of the abdominal viscera. This effect was also observed in healthy mice when the compound was injected by intraperitoneal route. In contrast, this delayed toxic effect was never encountered when the compound was administered by intravenous route. This type of toxicity seems to be correlated with the presence of 1,2-diaminocyclohexane (PHD, PHS, PHM, PHC and PHIC) since it was never observed with the diammino derivatives (PPD, PAC, PAIC).

The compounds PAC, PAIC and PHTA gave 17% (100 mg/kg), 74% (75 mg/kg) and 13% (500 mg/kg) of ILS in leukemia L 1210 ($10^5$ cells, intraperitoneal graft on $D_0$, treatment in one single injection on $D_1$). It is important to note the following:

(a) PHIC exerts the anti-tumour activity in leukemia L 1210 and sarcoma S 180, intraperitoneal graft, but causes peritonitis intraperitoneal treatment (Tables I and II).

(b) PHIC is active against leukemia L 1210 when the graft is intraperitoneal and the treatment is intravenous (Table III).

(c) The therapeutic index of PHIC, defined by the ratio T.I.=$LD_{50}$/MED (MED=Minimum effective dose, i.e., the dose corresponding to an ILS of 25% for both tumours) in 5.5 times greater than that of PDD in the case of leukemia L 1210 and 4.0 times greater in the case of sarcoma S 180.

TABLE I

COMPARED ANTI-TUMOUR ACTIVITY OF PDD AND PHIC AGAINST LEUKAEMIA L 1210 AND SARCOMA S 180

| | | L 1210[a] | | S 180[b] | |
|---|---|---|---|---|---|
| Compound | Dose (mg/kg) | ILS (%) | Survivals (%) | ILS (%) | Survivals (%) |
| PDD | 2 | 28 | — | — | — |
| | 4 | 52 | 0 | 41 | 0 |
| | 6 | 75 | 0 | — | — |
| | 8 | 106 | 0 | 65 | 0 |
| PHIC | 5 | 16 | 0 | — | — |
| | 10 | 40 | 0 | 29 | 0 |
| | 25 | 59 | 0 | 46 | 0 |
| | 50 | 79 | 0 | 112 | 20 |
| | 100[c] | 129 | 20 | 171 | 40 |

[a] i.p. graft ($10^5$ cells) on $D_0$ and i.p. treatment on $D_1$, 10 mice per dose average survival time for control animals: PDD = 9.3 ± 0.8 days; PHIC 8.6 ± 0.4 days
[b] i.p. graft ($10^6$ cells) on $D_0$ and i.p. treatment on $D_1$, 10 mice per dose average survival time for control animals: PDD = 17.1 ± 2.0 days; PHIC = 18.7 ± 1.3 days
[c] one toxic death excluded from ILS calculation

TABLE II

COMPARED ANTI-TUMOUR ACTIVITY AGAINST LEUKAEMIA L 1210 AND SARCOMA S 180

| | | L 1210 | | S 180 | |
|---|---|---|---|---|---|
| Compound | Dose (mg/kg) | ILS (%) | Survivals (%) | ILS (%) | Survivals (%) |
| PHD | 1 | 5 | 0 | 100 | 0 |
| | 2 | 49 | 0 | 128 | 20 |
| | 4 | 65 | 0 | 127 | 10 |
| PHM | 5 | — | — | 25 | 0 |
| | 10 | — | — | 36 | 0 |
| | 20 | — | — | 44 | 0 |
| | 40 | — | — | 60 | 0 |
| | 50 | 103 | 10 | 96 | 0 |
| PHS | 0.5 | — | — | 4 | 0 |
| | 1 | — | — | 10 | 0 |
| | 2 | — | — | 25 | 0 |
| | 4 | — | — | 47 | 0 |

TABLE II-continued

COMPARED ANTI-TUMOUR ACTIVITY AGAINST LEUKAEMIA L 1210 AND SARCOMA S 180

| Compound | Dose (mg/kg) | L 1210 ILS (%) | L 1210 Survivals (%) | S 180 ILS (%) | S 180 Survivals (%) |
|---|---|---|---|---|---|
| PHC | 5 | 112 | 40 | 112 | 10 |
|  | 10 | — | — | 20 | 0 |
|  | 25 | — | — | 124 | 20 |
|  | 50 | — | — | 121 | 30 |
|  | 100 | — | — | — | — |
|  | 120 | 90* | 0 | — | — |

*with 5 mice only
I.p. graft ($10^5$ cells for L 1210 tumour and $10^6$ cells for S 180 tumour) on $D_O$ and i.p. treatment on $D_1$, 10 mice per dose

TABLE III

ANTI-TUMOUR ACTIVITY OF PHIC AGAINST LEUKAEMIA L 1210 S.C. GRAFT - I.P. TREATMENT I.P. GRAFT - I.V. TREATMENT

|  | Subcutaneous Graft ($10^6$ cells)[a] |
|---|---|
| I.p. treatment on $D_1$ |  |
| 62.5 mg/kg | ILS 26 |
| I.p. treatment on $D_4$ |  |
| 62.5 mg/kg | 17 |
| 125 mg/kg | 50 |
|  | Intraperitoneal Graft ($10^5$ cells)[b] |
| I.v. treatment on $D_1$ | ILS |
| 50 mg/kg | 25 |
| 125 mg/kg | 41 |

[a] average survival time for control animals = 8.6 ± 0.5 days
[b] average survival time for control animals = 8.8 ± 0.7 days Comparative studies were also performed in order to evaluate the in vitro and in vivo toxicities of the compound PHIC of the invention. The results of the trials are summarized:

A. L 1210 CELLS IN CULTURE

In vitro toxicity was determined using L 1210 cells in culture by measuring the inhibitory dose 50, $ID_{50}$, which represents the concentration of the platinum compound which reduces by 50% the rate of growth of the cells after prolonged contact, usually 24 to 48 hours, with the compound to be tested. At the $ID_{50}$, all the cells were viable as judged by exclusion with trypan blue. The experimental part of this study is described in a recently published article (P. LECOINTE, J. P. MACQUET and J. L. BUTOUR (1979) Biochem. Biophys. Res. Commun., 90, 209-213). The results are shown in Table IV.

TABLE IV

CYTOTOXICITY OF THE DIFFERENT COMPOUNDS ON L 1210 CELLS IN CULTURE

| Compounds compared | $ID_{50}$ ($\mu M$) |
|---|---|
| PDD | 2.33 |
| PHD | 0.13 |
| PHS | 0.19 |
| PHM | 0.39 |
| PHIC | 0.42 |

B. TOXICITY IN THE MOUSE AND IN THE RAT.

1. Toxicity i.p., i.v. and p.o.

Acute toxicity, one single injection of the compound, was measured using Swiss female mice (Evic-Ceba, Bordeaux) of 21 to 23 g. and Sprague-Dawley rats. Ten animals were treated for each dose studied. The toxicity of the different compounds is given in Table V.

TABLE V

ACUTE TOXICITY OF THE DIFFERENT COMPOUNDS IN THE MOUSE

|  | PDD | PAC | PAIC | PHD | PHC | PHIC | PHTA |
|---|---|---|---|---|---|---|---|
| $LD_0$* (mg/kg) | 9 | 125 | 75 | 7 | 150 | 153 ($LD_{10}$)* | >500 |

$LD_0$* = maximum non-lethal dose;
$LD_{10}$ = dose killing 10% of the animals.

The toxicity by intraperitoneal (i.p., 10 animals per dose), intravenous (i.v., 10 animals per dose) and oral (p.o., 10 animals per dose) routes of PHIC is reported in Table VI. The loss of weight on the 4th day of the animals i.p. treated was 3.5 g of the $LD_{10}$ dose, 4.3 g for the $LD_{50}$ dose.

TABLE VI

TOXICITY BY INTRAPERITONEAL (I.P.), INTRAVENOUS (I.V.) AND ORAL (P.O.) ROUTES OF PHIC IN THE MOUSE AND RAT

| animal | route | $LD_{10}$ mg/Kg | $LD_{50}$ mg/Kg | $LD_{90}$ mg/Kg |
|---|---|---|---|---|
| mouse | I.P. | 135 | 236 (220-254)* | 365 |
|  | I.V. | 348 | 421 (411-431)* | 489 |
|  | P.O. | >1 000 |  |  |
| rat | I.P. | 61 | 143 (134-153)* | 278 |
|  | I.V. | 111 | 173 (156-192)* | 244 |
|  | P.O. | >1 000 |  |  |

$LD_{10}$ = dose killing 10% of the animals
$LD_{50}$ = dose killing 50% of the animals
$LD_{90}$ = dose killing 90% of the animals
*range corresponding to P = 0.05

It should be added that between 50 and 80% of the surviving animals at the i.p. treatment developed peritonitis as judged by adhesion and hardening of the abdominal viscera within the month following the injection of PHIC. As discussed above this problem seems to be linked to the presence of the 1,2-diaminocyclohexane ligand. When PHIC is injected intravenously this long-term toxic effect is not observed.

2. Renal and hepatic toxicity

The nephrotoxicity of PDD is well known. It was thus of interest to compare the effects of the novel compound of the invention with those of the already known compounds listed above on the kidney and the liver, i.e. the organs in which the greatest amount of platinum accumulates.

Swiss female mice (Evic-Ceba, Bordeaux) of 20 to 22 g were treated by intraperitoneal route $D_0$ and then sacrificed on $D_1$, $D_4$ and $D_{10}$. Nine mice were used per compound and the doses administered are given in Table VII.

TABLE VII

DOSES USED IN THE STUDY OF RENAL AND HEPATIC TOXICITY

| Compound | PDD | PAC | PHD | PHM | PHS | PHC | PHIC |
|---|---|---|---|---|---|---|---|
| Dose (mg/kg) | 8 | 100 | 4 | 50 | 5 | 120 | 150 |
| Solvent | 9‰ aqueous solution of NaCl | 9‰ aqueous solution of NaCl | 4‰ aqueous Klucel solution | 4‰ aqueous Klucel solution | $H_2O$ | $H_2O$ | 9‰ aqueous solution of NaCl |

It should be noted that these doses corresponded to the maximum non-toxic doses in the healthy mouse (~LD$_0$). The renal and hepatic parenchyma were observed in organs fixed with a Duboscq-Brasil mixture and embedded in paraffin. Slices 5 microns thick were coloured with hemalun eosine stain. In most cases, the alterations were located in the cortex and in the proximal and distal tubules. They were:

(a) Nuclear alterations:
marked anisocaryosis
alteration of the chromatin either washed out or lumpy with hyperchromatism and/or pyknosis
the nuclear membrane was irregular and sometimes incised (b) Alterations of the cytoplasm:
Anisocytosis with alteration of the brush border of the proximal tubules and intracytoplasmic eosinophilic inclusions.

Some scattered patches suggested isolated cellular necrosis in the proximal and distal tubules. In one case an abscess was observed on D$_{10}$ after treatment with PHM. Tubular dilation with hyaline casts in the nephron as a whole were found with, at times, a pseudovesicular aspect. These alterations, when they were observed, were at their maximum on D$_4$ and stabilized on D$_{10}$. Variations in the same series suggested variations in sensitivity.

These alterations were observed with:
(a) PDD (8 mg/kg), PAC (100 mg/kg) and PHM (50 mg/kg).
(b) PHD (4 mg/kg): vascular alterations without any hyaline casts.
(c) PHS (5 mg/kg): vascular dilation and proximal distorted tubules.

PHC (120/mg/kg) and PHIC (150 mg/kg) did not provoke any significant alterations on this type of preparation. The splenic and even suprarenal parenchyma which were sometimes dissected, showed no abnormalities.

From the foregoing it can be concluded that the novel compound of the invention, PHIC, does not cause any renal lesion even at a dost 20 times greater to that of PDD.

Comparative studies of the behavious of the compound of the invention, PHIC and of compound PDD have also been made with respect to cellular penetration in vivo in the mouse. The results are given below. DBA/2 mice received 10$^6$ L 1210 cells on D$_0$ and were treated three days later with an amount of platinum compound equal to the LD$_0$ in the healthy mouse. Two hours after treatment on D$_3$, the animals were sacrificed. About 20.10$^6$ cells were extracted from the peritoneum and washed several times so as to eliminate the extra-cellular platinum and also any intracellular platinum which was not bound in a covalent manner with the cellular organelles. Platinum was monitored by atomic absorption for whole cells and also on the DNA which was purified by phenol extraction. In the case of PDD (9 mg/kg) only 0.4% of the platinum injected into the animal entered the cells. This corresponds to 180.10$^{-16}$ g of platinum per leukemic cell. Under these conditions, one fixed platinum atom per 3000 nucleotides was found, i.e. a total of 1% of the amount which penetrated the cells was complexed to DNA. For animals treated with 150 mg/kg PHIC, 0.15% penetrated the cells, which corresponds to 700. 10$^{-16}$ of platinum per cell. For this compound one fixed platinum atom was found for 3500 nucleotides. As in the case of PDD, 1% of the amount of PHIC which entered the cells was complexed to DNA. The results are given in Table VIII.

TABLE VIII

COMPARISON OF THE PENETRATION OF PDD AND PHIC INTO L 1210 CELLS GRAFTED TO THE ANIMAL AND QUANTIFICATION IN THE DNA

| Platinum compound | Dose (mg/kg) | Amount of penetrating platinum per cell ($\times 10^{-16}$g) | Number of fixed platinum atoms per nucleotide on DNA |
|---|---|---|---|
| PDD | 9 | 180 | 1/30000 |
| PHIC | 150 | 700 | 1/3500 |

Finally, a preliminary toxicological study was conducted with PHIC in the baboon so as to determine the folowing parameters:
(a) Nephrotoxicity
(b) Hematotoxicity
(c) Gastro-intestinal toxicity
(d) Hepatic toxicity
(e) Ototoxicity
as well as the maximum non-lethal dose.

In order to find out the maximum tolerable dose, two baboons, identified by no 1 and no 2, received 100 mg/kg and 150 mg/kg respectively without prehydration. Hydration was performed on baboon no 3 which received a dose of 200 mg/kg.

| Baboon No | Weight (kg) | Dose (mg/kg) | Frequency of treatment |
|---|---|---|---|
| 1 | 8.4 | 100 | 1 at D$_0$<br>1 at D$_{37}$<br>1 at D$_{58}$<br>1 at D$_{84}$<br>1 at D$_{105}$<br>1 at D$_{133}$ |
| 2 | 7.3 | 150 | 1 at D$_0$ |
| 3 | 7.5 | 200 | 1 at D$_0$ |

The PHIC was dissolved in a 9% solution of sodium chloride at the concentration of 100 mg/ml and then filtered on a 0.22 microns millipore filter. The compound was injected into the femoral vein during 5 to 10 minutes. Baboon No. 3 (200 mg/kg) received 700 ml of physiological serum by intravenous route. Baboons Nos. 1 and 2 received 1000 ml by sub-cutaneous route.

Gastro-intestinal toxicity was the first type of toxicity to appear and generally manifested itself 1 to 2 hours after injection of the compound. In all instances, vomiting was not profuse and lasted between 4 and 5 hours. Blood samples were taken at regular intervals and the results are listed in Tables IX, X and XI. D$_0$ was the day of treatment and a sample was taken before the compound was injected.

The results on D$_0$ were therefore control values.
D$_1$ = first day after treatment,
D$_2$ = second day, etc.

Baboon No. 2 treated with 150 mg/kg PHIC died on D$_{11}$, most certainly from the nephrotoxicity of the compounds as indicated by a creatine level of 1552. This baboon had neither eaten nor drunk for 11 days. Prolonged hydration of the animal (2 to 3 days) by subcutaneous route was also tested but appeared not to be the best solution. At 100 mg/kg, under these conditions, no nephrotoxic effect was observed, in the absence of hydration. At a dose of 200 mg/kg with hydation, nephtotoxicity is detected but creatinine levels return to normal values on day 18.

An ototoxicity test was carried out on baboon No. 3 (200 mg/kg) on $D_{31}$. This test comprised the following: (a) Registering the auditory potentials when the ear was submitted to 1500 stimuli at 90, 80, 70, 60, 50, 40, 30, 20 and 10 decibels. The results gave the latency times for conduction from the ear to the brain. (b) Performing the same kind of test by echocochleography. This analysis was much more accurate than the previous one because it was only carried out in the Corti organ (cochlea). Frequencies of 8000, 4000, 2000 and 1000 Hertz at 90, 70, 50, 30, 20 and 10 decibels were used. Measurements were made using a Racia Medelec Empled $MK_4$ 1026. No ototoxic effect was detected at the dose of 200 mg/kg of PHIC. The properties of PHIC compared to those of PDD can be summarized as follows:

| | | PHIC | PDD |
|---|---|---|---|
| 1. | Hydrosolubility | unlimited (>1500 mg/ml) | 2 mg/ml |
| 2. | Anti-tumour properties | | |
| | (a) Therapeutic index | | |
| | L 1210 | 36.3 | 6.5 |
| | S 180 | 21.5 | 5.2 |
| | (b) Surviving animals having received L 1210 leukaemia and S 180 sarcoma | Yes | No |
| 3 | Nephrotoxicity | No | Yes |

| | PHIC | PDD |
|---|---|---|
| ($LD_0$ level, mice) | | |

The compound of the invention is superior to PDD by the criteria of solubility, toxicity and anti-tumor activity. (Cf. Tables IX, X and XI pp. 22, 23, 24, 25 and 26).

It will be recognized by one skilled in the art that the administrable amount depends on the seriousness of the condition to be treated and therefore is generally administered in that amount which is effective to control the tumours, which amount is in the range of 1 to 400 mg per kg of body weight per day.

For information relating to cancer and current forms of cancer treatment, the following publications are incorporated by reference:

Thorn, George W. et al., *Harrisons Principals of Internal Medicine*, Eighth Edition, McGraw-Hill, Inc. (New York, 1977) pp. 1731–1788).

Goodman, Louis S. et al. *The Pharmacological Basis of Therapeutics*, Fifth Edition, McMillan Publishing Co., Inc. (New York, 1975) pp. 1248–1253.

With regard to other platinum compounds having activity against leukemia L 1210, reference is made to NTIS document No. PB-299 427, (*N-phosphonacetyl-L-aspartate*) (1,2-*diamino-cyclohexane*) *platinum* (*II*) or *Alkali Metal Salt*, U.S. Ser. No. 6-058,287, filed July 7, 1979, by Meischen, Gale and Noff.

TABLE IX

ANALYSIS OF BABOON No 1: 100 mg/kg

| | $D_0$ (Control) | $D_1$ | $D_2$ | $D_6$ | $D_{16}$ | $D_{30}$ | $D_{37}$ | $D_{38}$ | $D_{41}$ | $D_{48}$ |
|---|---|---|---|---|---|---|---|---|---|---|
| QUICK PLASMA PROTHROMBIN TIME (100%) | 100 | 75 | 80 | 65 | 95 | 85 | 85 | 85 | 100 | 95 |
| FIBRINOGEN I (2–4 g/l) | 3.20 | — | 2.25 | 2.40 | 1.95 | 1.52 | 1.46 | 1.85 | 2.72 | 2.70 |
| PROACCLELERIN V (100%) | — | — | — | 100 | — | — | — | — | — | — |
| PROCONVERTIN VII + STUART FACTOR X (100%) | — | — | — | 70 | — | — | — | — | — | — |
| PROTHROMBIN II (100%) | — | — | — | 95 | — | — | — | — | — | — |
| CREATININE (53–130 μmols/l) | 117 | — | 110 | 91 | 105 | 138 | 99 | 85 | 102 | 136 |
| GRANULOCYTES (4000–7000) | 2550 | — | — | 2480 | 4560 | 3969 | 2989 | 4824 | 4212 | 3696 |
| PLATELETS (100000–250000) | 364000 | — | — | 526000 | 414000 | 414000 | 362000 | 299000 | 371000 | 708000 |
| WEIGHT (Kg) | 8.4 | — | — | 7.7 | 8.4 | — | 8.35 | — | — | 7.6 |

| | $D_{57}$ | $D_{58}$ | $D_{62}$ | $D_{76}$ | $D_{79}$ | $D_{84}$ | $D_{85}$ | $D_{90}$ | $D_{100}$ |
|---|---|---|---|---|---|---|---|---|---|
| QUICK PLASMA PROTHROMBIN TIME (100%) | 90 | — | 50 | 95 | 95 | — | 85 | — | 95 |
| FIBRINOGEN I (2–4 g/l) | 2.67 | — | 1.86 | 1.75 | 2.10 | — | 2.08 | — | 2.50 |
| PROACCELERIN V (100%) | — | — | — | — | — | — | 100 | — | — |
| PROCONVERTIN VII + STUART FACTOR X (100%) | — | — | — | — | — | — | 90 | — | — |
| PROTHROMBIN II (100%) | — | — | — | — | — | — | — | — | — |
| CREATININE (53–130 μmols/l) | 96 | — | 136 | 121 | 138 | — | 97 | 96 | 110 |
| GRANULOCYTES (4000–7000) | 2498 | — | 3726 | 1071 | 2541 | — | 3599 | 1917 | 3230 |
| PLATELETS (100000–250000) | 329000 | — | 378000 | 375000 | 382000 | — | 549000 | 685000 | 340000 |
| WEIGHT (Kg) | — | 8.45 | — | — | — | 7.93 | — | — | — |

TABLE IX-continued
ANALYSIS OF BABOON No 1: 100 mg/kg

| | $D_{105}$ | $D_{106}$ | $D_{111}$ | $D_{122}$ | $D_{129}$ | $D_{133}$ | $D_{134}$ | $D_{140}$ |
|---|---|---|---|---|---|---|---|---|
| QUICK PLASMA PROTHROMBIN TIME (100%) | 95 | 75 | 48 | 100 | 100 | — | — | 100 |
| FIBRINOGEN I (2–4 g/l) | 2.25 | 2.20 | 2.20 | 2.10 | 2.15 | — | — | 2.50 |
| PROACCELERIN V (100%) | — | — | 100 | — | — | — | — | — |
| PROCONVERTIN VII + STUART FACTOR X (100%) | — | — | 39 | — | — | — | — | — |
| PROTHROMBIN II (100%) | — | — | 70 | — | — | — | — | — |
| CREATININE (53–130 μmols/l) | 60 | 120 | 102 | * | 90 | — | 126 | 114 |
| GRANULOCYTES (4000–7000) | 2030 | 10120 | 1121 | 1232 | 5406 | — | 7245 | 4794 |
| PLATELETS (100000–250000) | 266000 | 231000 | 345000 | 348000 | 508000 | — | 580000 | 441000 |
| WEIGHT (Kg) | 8.59 | — | — | — | — | 7.65 | — | — |

$D_0$ = 1st injection, $D_{37}$ = 2nd injection.
$D_{58}$ = 3rd injection, $D_{84}$ = 4th injection.
$D_{105}$ = 5th injection, $D_{133}$ = 6th injection.
The values in brackets indicate the standards found in the human being.
*BUN = 4.5 mmol/l (normal range: 3–7 mmol/l).

TABLE X
ANALYSIS OF BABOON No 2: 150 mg/kg

| | $D_{00}$ (control) | $D_0$ (control) | $D_1$ | $D_4$ | $D_{11}$ |
|---|---|---|---|---|---|
| QUICK PLASMA PROTHROMBIN TIME (100%) | 95 | 90 | 60 | 85 | 55 |
| FIBRINOGEN I 2–4 g/l | 1.85 | 1.46 | 1.46 | 2.82 | 4.20 |
| PROACCELERIN V (100%) | — | — | 70 | — | 100 |
| PROCONVERTIN VII + STUART FACTOR X (100%) | — | — | 62 | — | 55 |
| PROTHROMBIN II (100%) | — | — | 42 | — | 55 |
| CREATININE (53–130 μmols/l) | 125 | 130 | 96 | 245 | 1552 |
| GRANULOCYTES (4000–7000) | 3072 | 6885 | 9672 | 1988 | 555 |
| PLATELETS (100000–250000) | 507000 | 293000 | 261000 | 212000 | 174000 |
| WEIGHT (Kg) | — | 7.3 | — | — | 5.5 |

$D_0$ = 1st injection. The values in brackets indicate the standards found in the human being.

TABLE XI
ANALYSIS OF BABOON No 3: 200 mg/kg

| | $D_0$ (Control) | $D_4$ | $D_6$ | $D_{12}$ | $D_{15}$ | $D_{18}$ | $D_{24}$ | $D_{30}$ | $D_{40}$ |
|---|---|---|---|---|---|---|---|---|---|
| QUICK PLASMA PROTHROMBIN TIME (100%) | 95 | 10 | 30 | 85 | 90 | 100 | 100 | 95 | 95 |
| FIBRINOGEN I (2–4 g/l) | 2.07 | 2.70 | 3.00 | 4.80 | 3.85 | 2.60 | 2.00 | 2.25 | 1.50 |
| PROACCELERIN V (100%) | — | 100 | 100 | — | — | — | — | — | — |
| PROCONVERTIN VII + STUART FACTOR X (100%) | — | <5 | 25 | — | — | — | — | — | — |
| PROTHROMBIN II (100%) | — | 30 | 25 | — | — | — | — | — | — |
| CREATININE (53–130 μmols/l) | 62 | 140 | 350 | 646 | 265 | 118 | 97 | 104 | 94 |
| GRANULOCYTES (4000–7000) | 3800 | 4536 | 5236 | 7905 | 3550 | 722 | 4872 | 10752 | 4731 |
| PLATELETS (100000–250000) | 241000 | 70000 | 208000 | 241000 | 114000 | 312000 | 366000 | 457000 | 299000 |

TABLE XI-continued

| | ANALYSIS OF BABOON No 3: 200 mg/kg. | | | | | | | | |
|---|---|---|---|---|---|---|---|---|---|
| | $D_0$ (Control) | $D_4$ | $D_6$ | $D_{12}$ | $D_{15}$ | $D_{18}$ | $D_{24}$ | $D_{30}$ | $D_{40}$ |
| WEIGHT (Kg) | 7.5 | 6.25 | — | 5.31 | — | — | 5.6 | 5.9 | 6.33 |

$D_0$ = 1st injection. The values in brackets indicate the standards found in the human being.

I claim:

1. Cis-isocitrato (1,2-diaminocyclohexane) platinum (II).

2. A process for forming cis-isocitrato (1,2-diaminocyclohexane) platinum (II) complex which comprises reacting a platinum atom which is partially chelated with 1,2-diaminocyclohexane together with trisodium isocitrate (dl-isomer).

3. A process according to claim 2 wherein cis-dichloro (1,2-diaminocyclohexane) platinum (II) is reacted with trisodium isocitrate.

4. A process according to claim 2, wherein cis-dichloro (1,2-diaminocyclohexane) platinum (II) is first reacted with silver nitrate to form the corresponding dinitratoplatinum compound which is thereafter reacted with trisodium isocitrate to form the required platinum complex.

5. In the process of claim 2 wherein the reaction is carried out in an aqueous medium and the platinum complex is formed including, the step of adding an organic solvent, whereby the recovery of an insoluble platinum complex is promoted.

6. The process of claim 2 which comprises carrying out the reaction at a temperature above room temperature.

7. The process of claim 6, which comprises prior, to adding the organic solvent, the step of removing part of the water from the reaction mixture.

8. The process of claim 5 in which the platinum complex is recovered in a yield of at least about 85%.

9. A process for preparing cis-isocitrato (1,2-diaminocyclohexane) platinum (II) complex which comprises reacting a compound of the formula:

cis—[Pt(1,2-diaminocyclohexane)(H$_2$O)$_2$](NO$_3$)$_2$ with trisodium isocitrate at a temperature of from about 60° to about 65° C. in water and then recovering the product formed.

10. The process of claim 9 wherein the product is recovered by the steps comprising concentrating the aqueous solution, filtering and then precipitating the product in a mixture of ethanol and acetone.

11. A therapeutic composition comprising the compound cis-isocitrato (1,2 diaminocyclohexane) platinum (II) complex for use in the treatment of tumors and a pharmaceutically acceptable carrier, the amount of said platinum II complex in the composition being a therapeutically effective amount and the composition being effective to inhibit L 1210 Leukemia or sarcoma 180 cells in baboons.

12. The therapeutic composition of claim 11 wherein the composition is in a dosage unit form suitable for oral, intramuscular or intravenous administration.

13. A pharmaceutical composition for inhibiting tumors in warm-blooded animals which comprises an effective amount of cis-isocitrato (1,2-diaminocyclohexane) platinum (II) in a pharmaceutically acceptable vehicle, which cis-isocitrato (1,2-diaminocyclohexane) platinum (II) is effective to inhibit tumors selected from the group consisting of leukemia L1210 or sarcoma S180 in baboons.

14. A therapeutic composition comprising the compound cis-isocitrato (1,2-diaminocyclohexane) platinum (II) in a therapeutically effective amount, and a pharmaceutically acceptable carrier, said compound being effective to inhibit sarcoma S 180, said composition being effective for inhibiting 1210 Leukemia or sarcoma 180 in baboons.

15. A method for use in the treatment of mammals which comprises administering to a mammal a therapeutically effective amount of a composition comprising cis-isocitrato (1,2-diaminocyclohexane) platinum (II) complex and pharmaceutically acceptable carrier, which composition is effective to inhibit L 1210 Leukemia cells in baboons.

16. The method of claim 15 wherein the administration is oral, intramuscular or intravenous.

17. The method of claim 16 wherein the composition is administered in a dosage range of 1 to 400 mg/kg of body weight per day.

18. A method of inhibiting tumors in a warm-blooded animal which comprises administering to said animal an effective amount of the composition of claim 13, which platinum compound is effective to inhibit L1210 cells the baboons.

19. A method of inhibiting tumors in a warm-blooded animal which comprises administering to said animal an effective amount of the composition of claim 13, which composition is effective to inhibit tumors selected from the group consisting of leukemia L1210 or sarcoma S180 in baboons.

20. A method for the treatment of mammals which comprises administering to a mammal an effective amount of a composition which comprises cis-isocitrato (1,2-diaminocyclohexane) platinum (II) complex in a therapeutically effective amount, and a pharmaceutically acceptable carrier, which composition is effective to inhibit sarcoma S 180 in baboons.

* * * * *